United States Patent [19]

Saeva et al.

[11] 3,931,041

[45] Jan. 6, 1976

[54] LIQUID CRYSTAL COMPOSITIONS

[75] Inventors: Franklin D. Saeva; Richard L. Schank, both of Webster, N.Y.

[73] Assignee: Xerox Corporation, Stamford, Conn.

[22] Filed: Feb. 14, 1974

[21] Appl. No.: 442,567

Related U.S. Application Data

[62] Division of Ser. No. 228,958, Feb. 24, 1972, Pat. No. 3,819,531.

[52] U.S. Cl. ....... 252/299; 23/230 LC; 252/408 LC; 350/150; 350/160 LC
[51] Int. Cl.² ... C09K 3/34; G02B 5/23; G02F 1/01; G02F 1/16
[58] Field of Search .................. 252/408 LC, 299; 350/160 LC, 150; 23/230 LC

[56] References Cited
UNITED STATES PATENTS

3,806,230  4/1974  Haas .............................. 252/408 LC

FOREIGN PATENTS OR APPLICATIONS

2,121,085  12/1971  Germany ............................ 252/299
2,026,280  12/1970  Germany ............................ 252/299

Primary Examiner—Benjamin R. Padgett
Assistant Examiner—T. S. Gron
Attorney, Agent, or Firm—James J. Ralabate; David C. Petre; Gaetano D. Maccarone

[57] ABSTRACT

Liquid crystalline compositions having the optical properties of the cholesteric mesophase are disclosed. The compositions comprise at least one nematic liquid crystalline material and at least one potentially cholesteric material which has a molecular structure which is similar to that of a nematic liquid crystal. Uses of the novel compositions are also described.

5 Claims, 1 Drawing Figure

U.S. Patent   Jan. 6, 1976   3,931,041
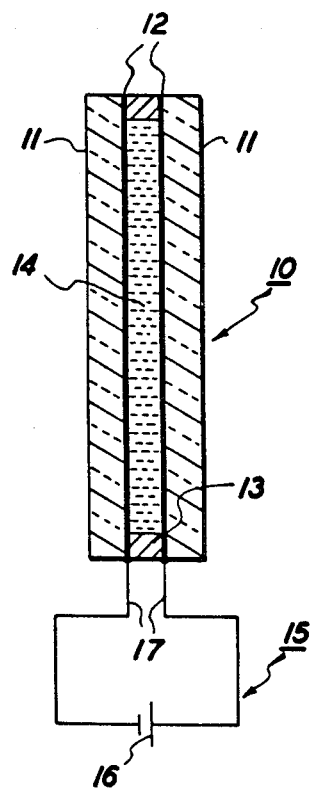

LIQUID CRYSTAL COMPOSITIONS

CROSS-REFERENCE TO RELATED APPLICATIONS

This application is a division of prior copending application Ser. No. 228,958, filed Feb. 24, 1972 now U.S. Pat. No. 3,819,531.

BACKGROUND OF THE INVENTION

This invention relates to liquid crystalline compositions and more specifically to liquid crystalline compositions having optically negative characteristics.

Recently there has been substantial interest in the discovery of more useful applications for the class of substances known as "liquid crystals." The name "liquid crystals" has become generic to liquid crystalline materials which exhibit dual physical characteristics, some of which are typically associated with liquids and others which are typically unique to solids. Liquid crystals exhibit mechanical characteristics, such as viscosities, which are ordinarily associated with liquids. The optical scattering and transmission characteristics of liquid crystals are similar to those characteristics ordinarily unique to solids. In liquids or fluids, the molecules are typically randomly distributed and oriented throughout the mass of the substance. Conversely, in crystalline solids the molecules are generally rigidly oriented and arranged in a specific crystalline structure. Liquid crystals resemble solid crystals in that the molecules of the liquid crystalline substances are regularly oriented in a fashion analogous to but less extensive than the molecular orientation and structure in a crystalline solid. Many substances have been found to exhibit liquid crystalline characteristics in a relatively narrow temperature range; but below such temperature ranges the substances typically appear as liquids.

Liquid crystals are known to appear in three different forms: the smectic, nematic and cholesteric forms. These structural forms are sometimes referred to as mesophases thereby indicating that they are states of matter intermediate between the liquid and crystalline states. The three mesophase forms of liquid crystals mentioned above are characterized by different physical structures wherein the molecules are arranged in a manner which is unique to each of the three mesomorphic structures. Each of these three structures is well known in the liquid crystal art.

Some liquid crystalline substances possess optically negative characteristics. Birefringence, also referred to as double refraction, is an optical phenomenon characteristic of some solid crystals and most liquid crystal substances. When a beam of unpolarized light strikes a birefringent substance it is split into two polarized components whose transverse vibrations are at right angles to each other. The two components are transmitted at different velocities through the substance and emerge as beams of polarized light. By the term "liquid crystalline substances which have optically negative characteristics," as used herein, is meant those for which the extraordinary index of refraction $\eta_E$ is smaller than the ordinary index of refraction $\eta_O$. Cholesteric liquid crystal substances exhibit this property. For a detailed description of this phenomenon see *Optical crystallography*, Wahlstrom, 4th Edition, Wiley and Sons, Inc., New York.

The molecules in cholesteric liquid crystals are arranged in very thin layers with the long axes of the molecules parallel to each other and to the plane of the layers within each layer. Because of the asymmetry and steric nature of the molecules the direction of the long axes of the molecules in each layer is displaced slightly from the corresponding direction in adjacent layers. This displacement is cumulative over successive layers so that overall displacement traces out a helical path. A comprehensive description of the structure of cholesteric liquid crystals is given in "*Molecular Structure and the Properties of Liquid Crystals*," G. W. Gray, Academic Press 1962.

Cholesteric liquid crystals have the property that when the propagation direction of plane polarized or unpolarized light is along the helical axis thereof, i.e., when the light enters in a direction perpendicular to the long axes of the molecules, (neglecting absorption considerations), this light is essentially unaffected in transmission through thin films of such liquid crystals except for a wavelength band centered about some wavelength $\lambda_o$ where $\lambda_o = 2np$ with $n$ representing the index of refraction of the liquid crystal substance and $p$ the pitch or repetition distance of the helical structure. The bandwidth $\Delta\lambda_o$ of this wavelength band centered about will typically be of the order of about $$\frac{\lambda_o}{14}.$$

For light of a wavelength $\lambda_o$, the cholesteric liquid crystal, under these conditions, exhibits selective reflection of the light such that approximately 50 percent of the light is reflected and approximately 50 percent is transmitted, assuming negligible absorption which is usually the case, with both the reflected and transmitted beams being approximately circularly polarized in opposite directions.

For light having wavelengths around $\lambda_o$ but not at $\lambda_o$ the same effect is present but not as pronounced. The transmitted light is not circularly polarized but is instead elliptically polarized. The cholesteric liquid crystals which exhibit this property of selective reflection of light in a region centered around some wavelength $\lambda_o$ are said to be in the Grandjean or "disturbed" texture. If $\lambda_o$ is in the visible region of the spectrum the liquid crystalline film appears to have the color corresponding to $\lambda_o$ and if $\lambda_o$ is outside the visible spectral region the film appears colorless.

Depending upon the intrinsic rotary sense of the helix, i.e., whether it is a right-handed or left-handed, the light that is transmitted in the region about $\lambda_o$ is either right-hand circularly polarized light (RHCPL) or left hand circularly polarized light (LHCPL). The transmitted light is circularly polarized with the same sense of polarization as that intrinsic to the helix. Thus, a cholesteric liquid crystal having an intrinsic helical structure which is left-handed in sense will transmit LHCPL and one having a helical structure which is right-handed in sense will transmit RHCPL.

Hereinafter these cholesteric liquid crystal substances will be identified, in order to conform with popular convention, by the kind of light which is reflected at $\lambda_o$. When a film is said to be right-handed, it is meant that it reflects RHCPL, and when a film is said to be left-handed, it is meant that it reflects LHCPL.

A right-handed cholesteric liquid crystal substance transmits LHCPL essentially completely at $\lambda_o$ whereas the same substance reflects almost completely RHCPL.

Conversely a left-handed film is almost transparent to RHCPL at $\lambda_o$ and reflects LHCPL. Since plane polarized or unpolarized light contain equal amounts of RHCPL and LHCPL, a cholesteric liquid crystal film is approximately 50% transmitting at $\lambda_o$ for these sources when the liquid crystal is in its Grandjean texture.

A further unique optical property of optically negative liquid crystal films is that contrary to the normal situation when light is reflected, such as by a mirror, where the sense of the circular polarization of the reflected light is reversed, this same phenomenon does not occur with light reflected by these liquid crystal films. The sense of the circular polarization of light reflected from these liquid crystal substances is not reversed but rather remains the same as it was before it came into contact with the liquid crystal substance. For example, if RHCPL having a wavelength $\lambda_o$ is directed at a right-hand film having $\lambda_o=2np$ it is substantially completely reflected and, after reflection, remains RHCPL. If the same light were to be directed on a mirror the reflected light would be LHCPL.

Because of these optical properties, optically negative liquid crystalline substances have been found to be highly advantageous for use in a number of varying applications. Copending patent applications Ser. No. 104,367 and Ser. No. 104,369, both filed Jan. 6, 1971, now U.S. Pat. Nos. 3,669,525 and 3,679,290 respectively disclose the use of such liquid crystalline materials in optical filter systems. The materials may be advantageously utilized in imaging methods such as are disclosed in copending application Ser. No. 821,565, filed May 5, 1969, now U.S. Pat. No. 3,652,148 and Ser. No. 867,593, filed Oct. 20, 1969, now U.S. Pat. No. 3,642,348. The thermal properties of these materials make them advantageous for use in thermometers, in detecting flaws in structural members, and in medical applications. Of course many other uses could be described but these should be sufficient to indicate the varied and important applications of optically negative liquid crystals.

In many of the applications cited above it would be desirable to have a liquid crystalline material which exists in the cholesteric mesophase at some temperature around room temperature (about 23°C); although there are also applications where it is to be desired to have the liquid crystalline material in this optically active state above room temperature or below room temperature. To achieve a material having a particular desired operational cholesteric mesomorphic temperature as well as other desired properties, e.g. a particular pitch or electric field sensitivity, it has heretofore been the usual practice to form compositions which are made up entirely of cholesteric liquid crystals or combinations of cholesterics and nematic liquid crystals or combinations of cholesterics and smectic liquid crystals.

Furthermore it has been found that considerable versatility can be achieved with respect to cholesteric liquid crystals by mixing together combinations of right-handed and left-handed cholesteric liquid crystals. In such a mixture there is a composition at which the right-handed and left-handed components nullify each other to provide an infinite pitch. This technique also makes it possible to generally achieve a broader range of pitches than typically can be achieved by mixing together only right-handed or only left-handed materials. See Proc. ACS Symposium on Ordered Fluids and Liquid Crystals, Sept. 1969, page 463.

Many left-handed cholesteric liquid crystal materials are known; however to date only relatively few right-handed materials have been provided. Thus there exists a continuing need for optically negative liquid crystalline compositions, particularly those which are right handed.

SUMMARY OF THE INVENTION

It is therefore an object of this invention to provide novel liquid crystalline compositions.

It is another object of the invention to provide liquid crystalline compositions which have the optical properties of the cholesteric mesophase.

It is a further object of the invention to provide liquid crystalline compositions having the optical properties of the cholesteric mesophase which are formed with at least one nematic liquid crystalline material and at least one potentially cholesteric material which has a molecular structure similar to that of nematic liquid crystals.

It is still another object of the invention to provide optically negative liquid crystalline compositions which are useful in electro-optic applications.

It is yet another object of the invention to provide optically negative liquid crystalline compositions which may be utilized in imaging and display devices.

The foregoing and other objects and advantages are accomplished in accordance with the invention by providing novel liquid crystalline compositions having the optical properties of the cholesteric mesophase which comprise at least one nematic liquid crystalline material and at least one potentially cholesteric material having a structure similar to that of a nematic liquid crystalline material. Thus, according to the invention it is possible to form liquid crystalline compositions having optically negative characteristics by combining two materials, neither of which itself forms a cholesteric mesophase.

The invention will be more fully understood from the following detailed description of various preferred embodiments thereof particularly when read in conjunction with the accompanying drawing wherein the FIGURE is a partially schematic cross-sectional view of a liquid crystalline imaging member.

These novel and advantageous compositions are typically prepared by heating a mixture of the individual components to the isotropic state, mixing the components thoroughly at this point and then allowing the mixture to cool. The existence of the optically negative characteristics can be determined by conventional microscopic analysis which shows, for example, cholesteric textures, a pitch band and extrinsic optical activity. Another technique for determining the existence of optically negative characteristics is described in copending application Ser. No. 191,671, filed Oct. 22, 1971.

This copending application generally relates to mixtures of cholesteric liquid crystalline materials and extrinsically optically inactive materials which become circularly dichroic when introduced into an optically negative environment. The existence of induced circular dichroism in the region of the absorption bands of the optically inactive additive materials has been found to be present only when a chiral arrangement of molecules, i.e., a helicoidal cholesteric mesophase, exists.

Any suitable nematic liquid crystalline material may be used in the novel compositions of the invention. Typical suitable nematic liquid crystalline materials include: p-azoxyanisole, p-azoxyphenetole, p-butoxybenzoic acid, p-methoxycinnamic acid, butyl-p-anisylidene-p'-aminocinnamate, anisylidene-p-aminophenylacetate, p-ethoxybenzylamino-a-methylcinnamic acid, 1,4-bis (p-ethoxybenzylidene) cyclohexane, 4,4'-dihexyloxybenzene, 4,4'-diheptyloxybenzene, anisal-p-aminoazobenzene, anisaldazine, a-benzeneazo (anisal naphthylamine), anisylidene-p-n-butylaniline, n,n'nonloxybenzyltoluldine, p-ethoxybenzylidene-p'-n-butylaniline and mixtures thereof.

Any suitable potentially cholesteric optically active material may be used in the compositions of the invention. These materials typically are chiral as single molecules because of molecular asymmetry or dissymmetry (racemic or non-chiral materials typically will not produce the desired effect;) should be soluble to at least some extent in the nematic liquid crystalline materials with which they are combined; and have a molecular structure which is rod-like, preferably one which possesses a relatively high degree of polarizability and conformational rigidity. Typical suitable potentially cholesteric optically active materials can be generally described as being represented by the general formulas $$W-Ar$$
$$\phantom{W-}\diagdown$$
$$\phantom{WWWW}X=Y$$
$$\phantom{WWWWWW}\diagdown$$
$$\phantom{WWWWWWWW}Ar-Z$$
or
$$W-Ar-Z \text{ or } W-Z$$

wherein X and Y are chosen from the following radicals:
  X = Y = CH
  X = CH, Y = N
  X = Y = N
  X = N, Y = N → O
  X = CH, Y = N → O
where W and Z can be the same or different radicals and can be a radical such as, alkenyl, alkynyl, alkoxy, halogen, alkyl, ester, nitro, cyano, amino, $(CH_3)_2N$, $RCO_2$, R—O—C, $RO(CH_2)_n$—O (where R = Straight or branched alkyl), n is any integer and where Ar may be

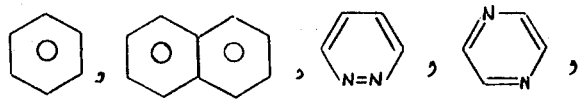

The concentration of each component may vary over an extremely wide range, e.g. from about 0.5 percent to about 98 percent by weight. Generally, the minimum and maximum amounts of the potential cholesteric, optically active material which may be incorporated in any composition are controlled primarily by the requirement that the composition must possess the optical properties of the cholesteric liquid crystal mesophase. Of course it will be recognized that the amount of the potentially cholesteric, optically active material typically required to obtain the desired properties in any composition can vary, this depending primarily on the material itself and the nematic liquid crystalline material with which it is combined.

Experimentation has shown that the interaction between the potentially cholesteric, optically active materials and the nematic liquid crystalline materials may, to some extent, be viscosity dependent. The potentially cholesteric optically active materials may be more effective with lower viscosity nematogenic materials. Low viscosity compositions may, in some embodiments be preferred for use in device applications since the molecules in these compositions may switch from one orientation to another more quickly. Thus there are provided advantageous low viscosity compositions having the optical properties of the cholesteric mesophase.

It has also been found that enantiomeric or mirror image, compositions may advantageously be prepared according to the invention. Enantiomeric compositions, left and right-handed helices respectively) can be prepared by adding enantiomeric potentially cholesteric, optically active materials having the opposite chirality to the same nematogenic material in accordance with the invention. For example, optically active S-ethyl-2-octyl carbonate can be combined with butyl (p-ethoxyphenoxy carbonyl) phenyl)carbonate (BPC) to form a mixture which has the optical properties of the cholesteric mesophase, possessing a right-handed helix and a pitch of about 5.0 μ. The optically active R-ethyl-2-octyl carbonate added to BPC also forms a mixture having the optical properties of the cholesteric mesophase, this composition having a left-handed helix and a pitch of about 5.0 μ.

It will be appreciated that this is an advantageous technique for preparing left and right-handed materials at will.

The novel compositions having the optical properties of the cholesteric mesophase may be advantageously employed in various electro-optic applications such as imaging and display devices. Copending patent application, Ser. No. 821,565, filed May 5, 1969, now U.S. Pat. No. 3,652,148 and hereby incorporated by reference herein discloses a system wherein an optically negative liquid crystalline substance is transformed to an optically positive liquid crystalline mesophase by an applied electric field. Copending patent application Ser. No. 867,593, filed Oct. 20, 1969, now U.S. Pat. No. 3,642,348 and hereby incorporated by reference herein discloses a system which transforms a cholesteric liquid crystalline material from its Grandjean or "disturbed" texture state to its focal-conic or "undisturbed" texture state by an applied electric field.

In FIG. 1 a typical liquid crystalline imaging member 10, sometimes referred to as an electroded imaging sandwich is shown in partially schematic cross-section where a pair of transparent plates 11 having substantially transparent conductive coating 12 upon the contact surface, comprise a parallel pair of substantially transparent electrodes. An imaging member wherein both electrodes are transparent is preferred where the imaging member is to be viewed using transmitted light; however a liquid crystalline imaging member may also be viewed using reflected light thereby requiring only a single transparent electrode while the other may be opaque. The transparent electrodes are separated by spacing member 13 which contains voids which form one or more shallow cups which contain the liquid crystalline film or layer 14 which comprises the active element of the imaging member. A field is created between the electrodes by an external circuit 15 which typically comprises a source of potential 16 which is connected across the two electrodes through leads 17. The circuit 15 may also contain suitable switching means. The potential source may be either A.C., D.C. or a combination thereof.

According to the system described in copending application Ser. No. 867,593, when cholesteric liquid crystals or a mixture of cholesteric liquid crystalline substances is used in an electrode sandwich such as described in FIG. 10, electrical fields applied across the liquid crystalline film cause an electrical field-induced texture transition to occur wherein a cholesteric liquid crystalline material initially in its Grandjean or "disturbed" texture is transformed to its focal-conic or "undisturbed" texture. The Grandjean texture is typically characterized by selective dispersion of incident light around a wavelength $\lambda_o$ (where $\lambda_o = 2np$ where $n = $ the index of refraction of the liquid crystalline film and $p = $ the pitch of the liquid crystalline film) and optical activity for wavelengths of incident light away from $\lambda_o$. If $\lambda_o$ is in the visible spectrum, the liquid crystalline film appears to have the color corresponding to $\lambda_o$, and if $\lambda_o$ is outside the visible spectrum the film appears colorless and non-scattering. The Grandjean texture of cholesteric liquid crystals is sometimes referred to as the "disturbed" texture.

The focal-conic texture is also typically characterized by selective dispersion but in addition this texture also exhibits diffuse scattering in the visible spectrum, whether $\lambda_o$ is in the visible spectrum or not. The appearance of the focal-conic texture state is typically milky-white when $\lambda_o$ is outside the visible spectrum. The focal-conic texture of cholesteric liquid crystals is sometimes referred to as the "undisturbed" texture.

For example, in this system when cholesteric liquid crystals are placed in the unbiased electrode sandwich, they initially appear colored, or colorless and transparent. If the electrode sandwich is observed between polarizers the imaging sandwich appears colored or black. When the electrical field is placed across the liquid crystalline film, the field-induced texture change is observable because the liquid crystalline film becomes white in the imaged area when the imaging sandwich is observed in transmitted or reflected light. The described imaging system thereby produces a white image on a dark or colored background. However, it is clear that either field or non-field areas in the liquid crystalline imaging sandwich may be used to create the desired image, with or without the use of polarizers or other image enhancing devices.

The system described in copending application Ser. No. 821,565, filed May 5, 1969 is similar to that just described but typically uses higher voltages and field strengths, (relative to those used in the system of application 867,593) to transform an optically negative liquid crystalline substance to an optically positive liquid crystalline mesophase. However, the respective processes produce entirely different effects as will be appreciated by those skilled in the art.

In the liquid crystal imaging member described in FIG. 10 the electrodes may be of any suitable transparent conductive material. Typical suitable transparent, conductive electrodes include glass or plastic substrates having substantially transparent and continuously conductive coatings of conductors such as tin, indium oxide, aluminum, chromium, tin oxide, or any other suitable conductor. These substantially transparent conductive coatings are typically evaporated onto the more insulating transparent substrate, NESA glass, a tin oxide coated glass manufactured by the Pittsburgh Plate Glass Co., is a commercially available example of a typical transparent, conductive electrode material.

The spacer, 13 in FIG. 10, which separates the transparent electrodes and contains the liquid crystal film between said electrodes, is typically chemically inert, transparent, substantially insulating and has appropriate dielectric characteristics. Materials suitable for use as insulating spacers include cellulose acetate, cellulose triacetate, cellulose acetate butyrate, polyurethane elastomers, polyethylene, polypropylene, polyesters, polystyrene, polycarbonates, polyvinylfluoride, polytetrafluoroethylene, polyethylene terephthalate, and mixtures thereof.

Such spacers, which also approximately define the thickness of the imaging layer of film of liquid crystals, are preferably of a thickness in the range of about 10 mils or less. Optimum results are typically attained with spacers in the thinckness range between about ¼ mil and about 5 mils.

It will be further recognized that the devices used in the imaging systems just described may be modified. For example, at least one of the electrodes shown in FIG. 10 may be provided in image configuration thereby providing a system where the desired image is defined by the shape of one of the electrodes, or the desired image may be defined by the shape of the spacing member; or at least one of the electrodes may also be a photoconductor and an imagewise field may be applied across the cholesteric liquid crystalline film by means of an imagewise pattern of activating radiation being directed upon the imaging cell while a potential is applied to the electrodes.

The invention will now be further described with respect to specific preferred embodiments thereof by way of Examples, it being understood that these are intended to be illustrative only and the invention is not limited to the materials, procedures, conditions, etc. recited therein. All parts and percentages recited are by weight unless otherwise specified.

EXAMPLE I 0.01 mole of p-n-butylaniline and 0.01 mole of (S)-p-sec-amyloxybenzaldehyde (previously prepared from the reaction of racemic (S)-sec. amyl alcohol with p-hydroxybenzaldehyde in the presence of base) are refluxed in 100 cc of absolute ethanol for about one hour after which the solvent is flash evaporated. The crude product is then distilled at 0.05 mm (204°–5°C) to give a yellow isotropic liquid which is (S)-p-sec.-amyloxybenzaldehyde-p-n-butylaniline anil (I). Analysis of the compound shows 81.97 percent C, 9.13 percent H and 4.16 percent N. $C_{22}H_{29}ON$ requires 81.68 percent C, 9.04 percent H and 4.33 percent N.

Compound I which does not possess any mesomorphic behavior is added to butyl(p-ethoxyphenoxy carbonyl phenyl)carbonate (BPC) to form a solution having a 10 percent concentration of I. The resulting mixture is heated at 100°C. until it is completely isotropic and then mixed thoroughly while it is in this state. The resulting supercooled mesomorphic material possesses the optical properties normally associated with the cholesteric mesophase, i.e., the existence of Grandjean and focal-conic cholesteric textures, a pitch band and extrinsic circular dichroism as determined by optical microscopy and by the use of a circular dichroism spectropolarimeter.

EXAMPLE II

Bis-((S)-sec. amyl-4,4'-azoxycinnamate (II) is prepared by the following technique. 0.10 mole of sec. amyl-4-nitrocinnamate (previously prepared from 4-nitrocinnamic acid chloride treated with (S)-sec. amyl alcohol in the presence of triethylamine) is suspended in 200 cc of water (The pH adjusted to 10 with ammonium hydroxide) along with 1.0 mole of sodium dithionite and stirred for about 2 hours at about 25°C. The crude hydroxylamine is collected by suction filtration and recrystallized from hexane.

0.05 mole of the hydroxylamine is then dissolved in 100cc of absolute ethanol and the reaction mixture is refluxed for about 5 hours. The crude axoxy compound (II) crystallizes from the reaction mixture on cooling and is collected by suction filtration and then recrystallized from absolute ethanol. Analysis of the compound shows 70.59 percent C, 7.04 percent H, 5.58 percent N. $C_{28} H_{34} N_2 O_5$ requires 70.27 percent C, 7.16 percent H and 5.85 percent N.

Compound (II), which forms only a smectic mesophase between about 125 and 162.5°C, is added to 4,4-diheptyloxyazoxybenzene, a nematic material commercially available from Eastman Kodak to make a solution having a 50 percent concentration of (II). The resulting mixture is heated at 170°C until it is completely isotropic and mixed thoroughly while it is in this state. The composition possesses the optical properties normally associated with cholesteric mesophases, i.e., cholesteric textures, a pitch band and extrinsic circular dichroism as determined by the techniques previously described.

The racemic form of compound (1), described in Example I, is added to the 4,4-diheptyloxyozoxybenzene. The resulting composition does not possess the optical properties of the cholesteric mesophase.

EXAMPLES III-XI

The compositions formed in these examples possess the optical properties normally associated with the cholesteric mesophase, i.e., the existence of cholesteric textures, a pitch band and extrinsic circular dichroism as determined by the techniques previously described.

EXAMPLE III

A composition comprising about 5 percent p-(S)-sec. amyloxybenzylidene-p-butylaniline and about 95 percent BPC.

EXAMPLE IV

A composition comprising about 5 percent (R)-2 octylethylcarbonate and about 95 percent BPC. The composition is found to be right-handed.

EXAMPLE V

A composition comprising about 5 percent of (S)-2-octylethylcarbonate and about 95 percent BPC. The composition is found to be left-handed.

EXAMPLE VI

A composition comprising about 10 percent (S)-sec. amyl-p-aminocinnamate and about 90 percent BPC. The composition is found to be right-handed.

EXAMPLE VII

A composition comprising about 10 percent (R)-2-octyl-p-aminobenzoate and about 90 percent BPC. The composition is found to be right-handed.

EXAMPLE VIII

A composition comprising about 10 percent (S)-2-octyl-p-aminobenzoate and about 90 percent BPC. The composition is found to be left-handed.

EXAMPLE IX

A composition comprising about 10 percent (S)-sec. amyl-p-aminobenzoate and about 90 percent BPC. The composition is found to be right-handed.

EXAMPLE X

A composition comprising about 10 percent (S)-2-octyl-p-aminocinnamate and about 90 percent BPC. The composition is found to c left-handed.

EXAMPLE XI

A composition comprising about 10 percent (R)-2-octyl-p-aminocinnamate and about 90 percent BPC. The composition is found to be right-handed.

Although the invention has been described in detail with respect to various preferred embodiments thereof it is not intended to be limited thereto but rather it will be appreciated by those skilled in the art that modifications and variations are possible which are within the spirit of the invention and the scope of the claims.

What is claimed is:

1. An imaging method comprising the steps of
 a providing an imaging member comprising a layer of a liquid crystalline composition having the optical properties of the cholesteric liquid crystalline mesophase, said composition consisting essentially of at least one nematic liquid crystalline material and at least one structurally similar non-mesomorphic optically active material which is represented by a general formula selected from the group consisting of
 W-Ar-Z, and
 W-Ar-X = Y-Ar-Z
 where X and Y are radicals chosen from the group consisting of
 X = Y = CH
 X = CH, Y = N
 X = Y = N
 X = N, Y = N    O
 X = CH, Y = N    O
 where W and Z can be the same or different and are chosen from the group consisting of $NH_2$ and alkenyl, alkynyl, alkoxy, alkyl, ester, carbonate, and aldehyde radicals having up to and including nine carbon atoms, and where Ar is chosen from the group consisting of

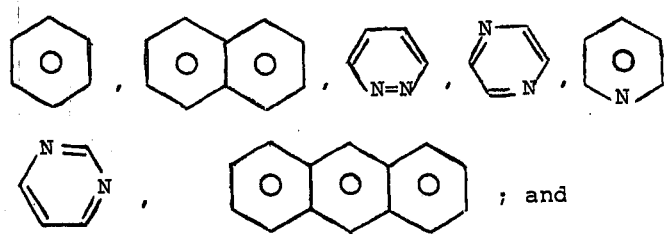
; and b applying an electrical field in imagewise configuration across said layer whereby the image portions of said layer are distinguishable from the background portions of said layer.

2. The imaging method as defined in claim 1 wherein said imaging member further includes a pair of electrodes and said liquid crystalline layer is arranged between said electrodes, wherein at least one of said electrodes is substantially transparent.

3. The imaging method as defined on claim 2 wherein at least one of said electrodes is shaped in image configuration.

4. An imaging method comprising the steps of a providing an imaging member comprising a layer of a liquid crystalline composition having the optical properties of the cholesteric liquid crystalline mesophase shaped in imagewise configuration, said composition consisting essentially of at least one nematic liquid crystalline material and at least one structurally similar non-mesomorphic optically active material which is represented by a general formula selected from the group consisting of W-Ar-Z, and
W-Ar-X = Y-Ar-Z where X and Y are radicals chosen from the group consisting of

X = Y = CH
X = CH, Y = N
X = Y = N
X = N, Y = N → O
X = CH, Y = N → O where W and Z can be the same or different and are chosen from the group consisting of $NH_2$ and alkenyl, alkynyl, alkoxy, alkyl, ester, carbonate, and aldehyde radicals having up to and including nine carbon atoms, and where Ar is chosen from the group consisting of

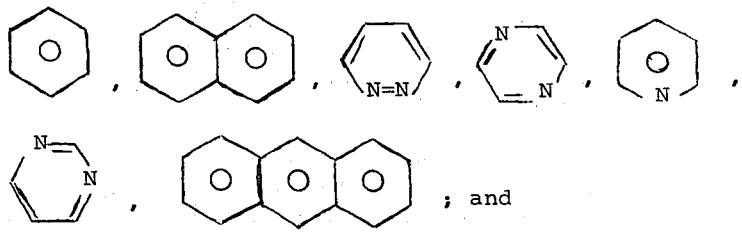 ; and b applying an electrical field across said layer whereby an image is observed.

5. The imaging method as defined in claim 4 wherein said imaging member further includes a pair of electrodes and said liquid crystalline layer is arranged between said electrodes, wherein at least one of said electrodes is substantially transparent.

* * * * *